United States Patent [19]
Roberge et al.

[11] Patent Number: 6,154,750
[45] Date of Patent: Nov. 28, 2000

[54] METHOD AND SYSTEM FOR NAVIGATION AND DATA ENTRY IN HEIRARCHICALLY-ORGANIZED DATABASE VIEWS

[75] Inventors: James Roberge, Damen; Jeffrey Soble, Highland Park, both of Ill.

[73] Assignee: Cyberpulse LLC, Highland Park, Ill.

[21] Appl. No.: 09/053,304

[22] Filed: Apr. 1, 1998

[51] Int. Cl.$^7$ .................................................. G06F 17/30
[52] U.S. Cl. ........................... 707/104; 707/1; 705/2; 705/3; 345/356; 345/357
[58] Field of Search .................. 345/357, 356; 707/501, 513, 100–103, 104; 705/2, 3, 6

[56] References Cited

U.S. PATENT DOCUMENTS

| | | | |
|---|---|---|---|
| 5,226,117 | 7/1993 | Miklos | 345/326 |
| 5,241,624 | 8/1993 | Torres | 345/326 |
| 5,247,666 | 9/1993 | Buckwold | 707/1 |
| 5,263,174 | 11/1993 | Layman | 345/356 |
| 5,307,262 | 4/1994 | Ertel | 705/2 |
| 5,379,422 | 1/1995 | Antoshenkov | 707/1 |
| 5,412,766 | 5/1995 | Bloomfield et al. | 345/357 |
| 5,425,140 | 6/1995 | Bloomfield et al. | 345/557 |
| 5,504,850 | 4/1996 | Aoyama | 345/356 |
| 5,715,449 | 2/1998 | Peters et al. | 707/104 |
| 5,801,702 | 9/1998 | Dolan et al. | 345/357 |
| 5,812,134 | 9/1998 | Kotchey | 345/356 |
| 5,812,135 | 9/1998 | Pooser et al. | 345/356 |
| 5,905,498 | 5/1999 | Diamont | 345/356 |
| 5,940,831 | 8/1999 | Takano | 707/10 |
| 5,950,168 | 9/1999 | Simborg et al. | 705/3 |
| 5,953,017 | 9/1999 | Beach et al. | 345/440 |
| 5,953,724 | 9/1999 | Lowry | 707/102 |

*Primary Examiner*—Hosain T. Alam
*Attorney, Agent, or Firm*—Fitch, Even, Tabin & Flannery

[57] ABSTRACT

A method and system for navigating hierarchical database views that supports the efficient entry, review, and updating of data using a navigation display that is clear and efficient—yet compact in terms of the screen area used. At any point in the navigation process, the navigation display consists of buttons corresponding to the nodes that lie along the path to the last node visited (the set of previously made choices) and the children of this node (the set of current choices). Unselected and unselectable choices are culled and do not clutter the display. The user navigates up and down the hierarchy and enters data by selecting these buttons. An important feature of the invention is support for multiple instances of database subhierarchies within this navigation process and display. In addition, multiple nodes can be composed to form a single database entry, thereby reducing the size and complexity of the hierarchical database views. Finally, database views that are directed acyclic graphs are also supported—including both serial and parallel traversal techniques.

61 Claims, 21 Drawing Sheets

Node tuple set

| 51 Identifier | 52 Label | 53 Description | 54 Type | 55 Instance |
|---|---|---|---|---|
| 1 | "Cardiac" | "Cardiac clinical data" | — | — |
| 11 | "Symptoms" | "Symptoms" | — | — |
| 111 | "Chest pain" | "Chest pain" | — | Auto |
| 112 | "Fatigue" | "Fatigue" | — | Auto |
| 12 | "Tests" | "Tests" | — | — |
| 121 | "Cath" | "Cardiac catheterization" | — | Auto |
| 122 | "Echo" | "Echocardiogram" | — | Auto |
| 1221 | "Left ventricle" | "Left ventricle" | — | — |
| 12211 | "Size" | "LV size" | Number | — |
| 12212 | "Thickness" | "LV thickness" | Number | — |
| 12213 | "Function" | "LV function" | — | — |
| 122131 | "Normal" | "LV function normal" | Finding | — |
| 122132 | "Hypo" | "LV function hypokinetic" | Finding | — |
| 122133 | "Hyper" | "LV function hyperkinetic" | Finding | — |
| 1222 | "Right Ventricle" | "Right ventricle" | — | — |
| 12221 | "Size" | "RV size" | Number | — |
| 12222 | "Thickness" | "RV thickness" | Number | — |
| 12223 | "Function" | "RV function" | — | — |
| 122231 | "Normal" | "RV function normal" | Finding | — |
| 122232 | "Hypo" | "RV function hypokinetic" | Finding | — |
| 122233 | "Hyper" | "RV function hyperkinetic" | Finding | — |
| 1223 | "Cardiomyopathy" | "Cardiomyopathy" | Finding | — |
| 123 | "Stress" | "Stress test" | — | Auto |
| 13 | "Labs" | "Lab results" | — | — |
| 131 | "Protime" | "Protime" | Number | Auto |
| 14 | Medications" | "Medications" | — | — |
| 141 | "Aspirin" | "Aspirin" | Dose | Auto |
| 142 | "Warfarin" | "Warfarin" | Dose | Auto |

Event tuple set

| Event Identifier | Node Identifier | Date |
|---|---|---|
| 1 | 11 | 2/24/97 |
| 2 | 122 | 5/1/97 |
| 3 | 142 | 9/1/97 |
| 4 | 131 | 10/5/97 |
| 5 | 142 | 11/4/97 |
| 6 | 11 | 11/16/97 |
| 7 | 122 | 11/16/97 |

Fig. 6a

Result tuple set

| Node Identifier | Event Identifier | Result |
|---|---|---|
| 11 | 1 | "Symptoms: Tires easily" |
| 12211 | 2 | "LV size 50 cm" |
| 12212 | 2 | "LV thickness 10 mm" |
| 122132 | 2 | "LV function hypokinetic" |
| 12221 | 2 | "RV size 20 cm" |
| 122231 | 2 | "RV function normal" |
| 142 | 3 | "Warfarin 2.0 mg" |
| 131 | 4 | "Protime 12 sec" |
| 142 | 5 | "Warfarin 2.5 mg" |
| 11 | 6 | "Symptoms: Absent" |
| 12211 | 7 | "LV size 55 cm" |
| 122132 | 7 | "LV function hypokinetic" |

Fig. 6b 201  function navigate ()
{
   // Pseudocode showing how the navigation process is
   // initiated and continued.

202     Let P = { root node }.
        Let C = { children of the root node }.

203     loop
            generate_structure ( P, C )
        until  ( the *Close* button on the button corresponding to the
                root node is selected )
    }

204  function generate_structure ( P, C )
{
   // Pseudocode showing the display and input processing that
   // takes place to generate the navigation structure
   // corresponding to ordered sets P and C, where $P = \{P_1, P_2, ..., P_n\}$
   // is an ordered set of nodes and $C = \{C_1, C_2, ..., C_m\}$ is the
   // ordered set of children of node $P_n$.

205     for   ( each node $P_i$ in P ) do
        {
            if ( i = 1 )
                Display a button for node $P_1$ in the upper, left-hand corner.
            else
                Display a button for node $P_i$ below and to the right of the button
                    for node $P_{i-1}$.
        }

206     for   ( each node $C_k$ in C ) do
        {
207         if  ( $C_k$ is the source of a serial link to some node $Q_{k'}$ )
                Let $C_k = Q_{k'}$.
            if  ( k = 1 )
                Display a button for node $C_k$ below the button for node $P_n$.
            else
                Display a button for node $C_k$ below the button for node $C_{k-1}$.

208         if  ( there is a result in the database that is associated with the
                    current instance of node $C_k$ )
                Display the result on button $C_k$.
        }
209     loop
        until ( the user presses a button )

2010    update_sets ( P, C, button_pressed )
    }

Fig. 20

```
211  function update_sets ( P, C, button_pressed )
     {
         // Pseudocode showing how ordered sets P and C are updated
         // in response to the user selecting the button denoted by
         // button_pressed.

212      if ( button for a node P_j was selected )
         {
213          Let P = {P_1,P_2,...,P_j}.
214          if ( j > i_open )
             {
                 Close the current open instance.
215              if ( parallel navigation structures are open )
                     Close them also.
             }
         }
216      else if ( button for a node C_k was selected )
         {
217          if ( C_k is an automatic trigger for opening an instance )
             {
                 Display the date selection tool and open an instance of
                     the subtree whose root is node C_k.
218              Let P_{n+1} = C_k.
219              Let C = { child nodes of P_{n+1} }.
2110             Let i_open = n + 1.
             }
2111         if ( node C_k is a finding )
                 Store the associated result in the database.
2112         else if ( node C_k is a predefined type )
             {
                 Display the corresponding input tool.
                 Store the input value in the database.
             }
2113         if ( C_k has children and i_open is not equal to n + 1 )
             {
2114             Let P_{n+1} = C_k.
2115             Let C = { child nodes of P_{n+1} }.
             } if ( C_k is the source of a parallel link to some node Q_{k'} )
             {
2116             Display a new (parallel) navigation structure using
                     ordered sets Q = {Q_1,Q_2,...,Q_k'} and D = {D_1,D_2,...,D_m'},
                     where {Q_1,Q_2,...,Q_{k'-1}} is the set of nodes on the path
                     to node Q_{k'} and {D_1,D_2,...,D_m'} is the set of children of
                     node Q_{k'}.
             }
         }
     }
```

Fig. 21

METHOD AND SYSTEM FOR NAVIGATION AND DATA ENTRY IN HEIRARCHICALLY-ORGANIZED DATABASE VIEWS

BACKGROUND OF THE INVENTION

1. Field of the Invention This invention relates to computer database systems in general and to the entry, update, and review of data in hierarchically-organized database views in particular.

2. Background of the Invention

One of the most challenging problems a software developer faces when designing a database system is creating a data entry mechanism that allows users to efficiently record information. In many environments, users operate under significant time pressures and are unwilling or unable to spend time on laborious data entry procedures. In order for a data entry mechanism to be effective, it must be fast, complete, and reconfigurable. In many cases, the data entry mechanism must also map onto small display screens or onto limited space within larger screens. This requirement has become increasingly important as more and more users take their computer systems with them as they move between work environments throughout the day. These highly mobile computing systems (e.g., hand-held computers) require data entry mechanisms that use screen space very economically. The same is true when data entry is performed within the context of screen-intensive imaging and graphics applications—when entering data while viewing digitized X-ray images, for example.

Most existing database systems use a forms-based data entry mechanism. Unfortunately, forms-based techniques fail to satisfy the requirements listed above. Most databases include a large number of fields (categories) and elements. Since the number of fields that can be displayed on a form at any one time is very small, a user must navigate through multiple complex forms in order to enter data. In addition, forms-based systems are difficult, if not impossible, to reconfigure without programming.

Some existing database systems use data navigation mechanisms that are based on hierarchically-organized views of the data. Note that we are discussing how the data is viewed, not how the data is structured within the database. Hierarchical views can be created for a variety of data structures (e.g., relational tables, hierarchical data structures, and network data structures).

One set of prior art techniques for navigating through hierarchically-organized database views is based on a diagrammatic representation of the hierarchy as a whole (FIG. 1). In these techniques, a user moves around the hierarchy by selecting nodes on the diagram using a mouse or other pointing device. Since the hierarchy is very large, only those nodes that lie near the last node selected are displayed (FIG. 2). The user can manually move the viewing window around (using scroll bars, for instance) and can reveal or hide levels of the hierarchy diagram by manually opening or closing nodes.

These techniques are designed to allow a user to view data elements in the context of the overall structure of the hierarchy and to visualize the logical relationships between data elements. However, the emphasis on overall structure makes these approaches ill-suited to the task of data entry. As the user moves down the hierarchy, he sees not only the nodes that represent possible choices for the next selection, but also large amounts of information that are irrelevant to the current data being entered. In addition, because much of the hierarchy diagram must, by necessity, be off-screen at any point in time, it is often difficult for the user to ascertain how he has reached a particular point in the hierarchy or how the displayed information fits within the overall structure.

A second set of prior art techniques for navigating through hierarchically-organized database views restrict navigation to movement up and down along the branches in the hierarchy. The contents of the levels that lie along the current branch are then displayed as cascading windows 31 or menu lists 32 (FIG. 3). An example of this kind of system can be found in U.S. Pat. No. 5,715,449 to Peters et al., which discloses a browser tree structure for limiting how information is entered into a medical database. In the preferred mode, the system presents the person inputting the data with a limited number of choices of data to be entered, from which the operator selects specific phrases descriptive, for example, of the health care provider's observations or instructions. These techniques improve somewhat the ease with which a user can identify the current set of choices by placing possible candidates in the topmost window or rightmost list. However, these techniques are still unnecessarily wasteful of screen space. Much of the screen is cluttered with unselected choices at each of the levels that lie along the current branch. Equally important, navigation remains difficult because important navigational guides for moving back up the hierarchy—the nodes selected along the current path, for instance—are frequently hidden under a window or pushed off-screen entirely.

Also, present navigational techniques for hierarchical file directory structures that display the names of the files in a selected directory along with the path to that directory are limited to file selection, and do not address the entry or review of database information.

OBJECTS OF THE INVENTION

An object of the present invention is to enhance the entry, update, and review of data in hierarchically-organized database views by presenting a user with a compact navigation display in which the current set of choices is clearly identified, along with the path through the hierarchy leading to these choices.

Another object of the present invention is to allow a user to create and access multiple instances (values) of the nodes and subhierarchies in a database view using this navigation process and display.

Another object of the present invention is to support the creation of individual database entries from multiple nodes by allowing a user to use this navigation process and display to enter data for a set of nodes and to compose this data into a single database entry.

Another object of the present invention is to support the navigation of links between nodes that occur on separate branches in the hierarchy (and which transform the hierarchy tree into a directed acyclic graph), where this navigation can be done in either a serial or parallel manner.

Another object of the present invention is to allow a user to use this navigation process and display to efficiently integrate, navigate, and comment upon information that includes a wide range of data types—e.g., text files, HTML (Hyper-Text Markup Language) documents, audio data, and image data—where this information can reside on a local area network, a corporate intranet, or the world-wide Internet.

SUMMARY OF THE INVENTION

These and other objects are achieved in the present invention by a set of integrated navigation, display generation, data entry, and data review methods. These methods work in concert to allow a user to move efficiently through a hierarchically-organized database view for the purposes of entering, reviewing, and updating data. Equally important, these methods produce a screen display that is highly economical in its use of screen real estate.

At each step in the data entry process (FIG. 9), the user sees buttons 91 corresponding to the choices she has made along with buttons 93 corresponding to the candidates for the next choice to be made. As a result, the screen is free of the clutter characteristic of existing techniques (FIG. 2 and FIG. 3). In particular, the user does not see—and screen space is not wasted on—the display of unselected (and unselectable) choices. The user's ability to navigate the hierarchy is unhindered, however. At any point in the data entry and review process, the user can move back up the hierarchy (i.e., retrace her steps) simply by reselecting a button 91 corresponding to a previously made choice or move down the hierarchy by selecting a button 93 from among the current set of choices.

Note that these methods do not simply support the navigation of static data structures. A hierarchical database view contains multiple instances of various subhierarchies. FIG. 4, for example, shows a view containing multiple echocardiographic reports (42 and 44)—each with its own unique date-stamp. The methods in the present invention seamlessly blend the selection of subhierarchy instances (e.g., echocardiographic reports) into the navigation process and display outlined above. In other words, these methods support navigation of both the structural (FIG. 9) and the temporal (FIG. 10) components of a database.

Nor are these methods limited to use with hierarchical views in which each entry in the database corresponds to a single node in the hierarchy. Such views can easily become quite large and unwieldy (both for the database system and the user). The methods in the present invention support hierarchical views in which the values assigned to several nodes combine to define a single database entry. The user simply inputs values for the nodes and the database entry is automatically constructed and stored.

In addition, the methods in the present invention are not restricted to database views that are trees (i.e., limited to having only a single path between nodes). These methods fully support database views that are directed acyclic graphs by allowing for additional links between nodes. These links can then be traversed—and displayed—as either serial or parallel structures, as shown in FIGS. 18 and 19, respectively.

Finally, the methods in the present invention are not limited to marked/unmarked (i.e., yes/no) data items. The preferred embodiment of the present invention, for example, supports a diverse set of data types—including numbers, dates, prescription doses, file names, Universal Resource Locators (URLs), and free-text comments. All of these data types may be input and reviewed within the context of the hierarchical navigation process and display outlined above.

DEFINITIONS

FIG. 1 shows a hierarchically-organized database view. Consistent with the accepted terminology in the field, we will refer to the hierarchy as a tree, to the topmost node in the hierarchy as the root node, to the path from the root node to any other node as a branch, and to a subset of the hierarchy that is itself a hierarchy as a subtree.

FIG. 4 shows sample database contents for the hierarchically-organized database view depicted in FIG. 1. The database contents are depicted as nodes or subtrees. Consistent with the accepted terminology in the field, we will refer to the data values for a node as instances of that node and the data values for a subtree as instances of that subtree. For example, node instance 41 represents the Warfarin dose recorded on 9/1/97 and subtree instance 42 represents the data recorded for the echocardiogram given on 5/1/97. Although date stamps are used to distinguish instances in the preferred embodiment of the invention, alternative schemes for uniquely identifying node and subtree instances could easily be used instead.

BRIEF DESCRIPTION OF THE DRAWINGS

FIG. 5 is a diagram showing the node tuple set used in the preferred embodiment of the present invention to represent the database view depicted in FIG. 1.

FIGS. 6a and 6b are schematic diagrams showing the event and result tuple sets used in the preferred embodiment of the present invention to store the node and subtree instances depicted in FIG. 4.

FIG. 20 is a pseudocode example showing how the navigation process can be initiated and continued.

FIG. 21 is a pseudocode example showing how the navigation process can be initiated and continued.

DETAILED DESCRIPTION OF A PREFERRED EMBODIMENT OF THE INVENTION

Figure 1:
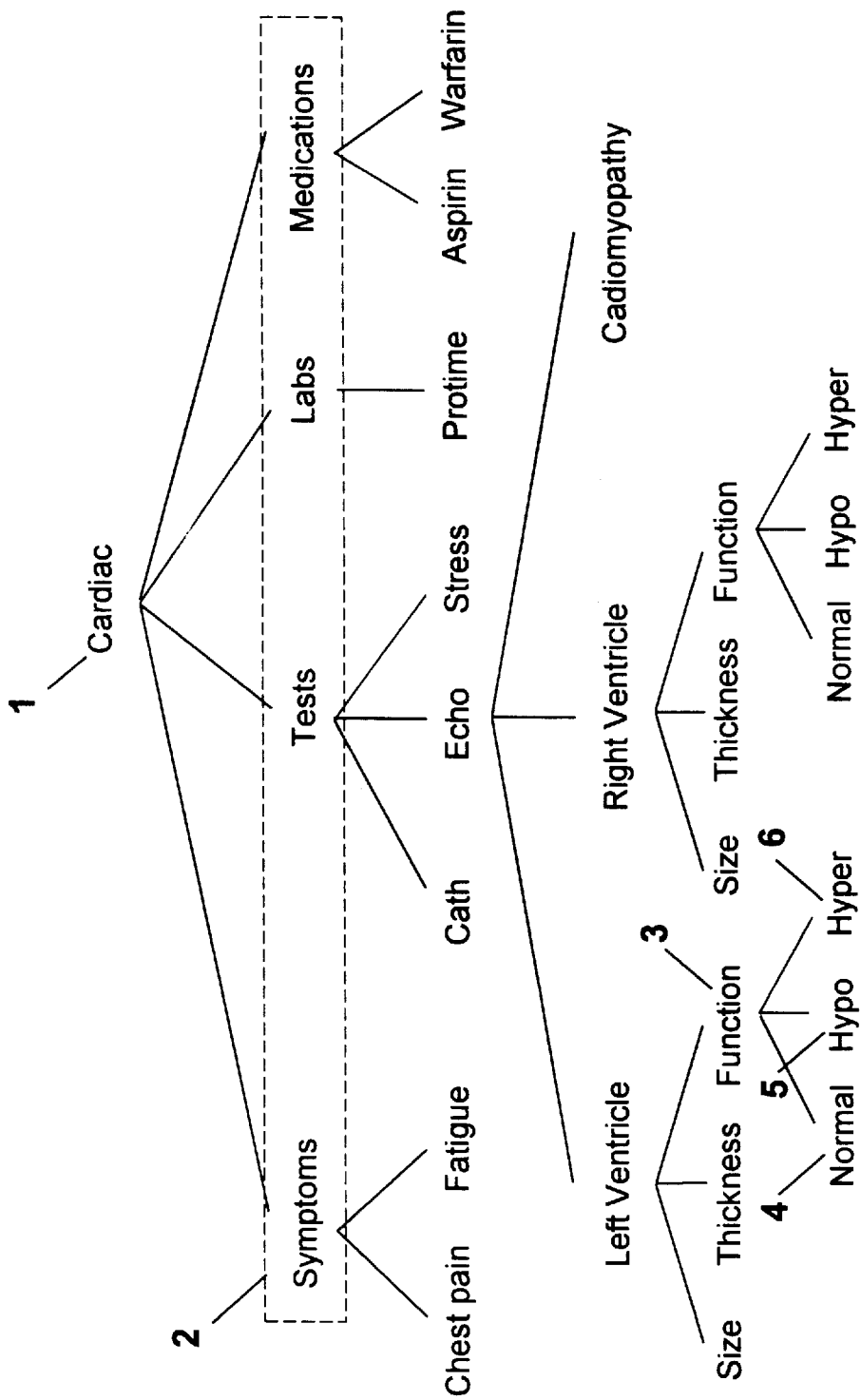
FIG. 1 is a schematic diagram showing the hierarchical relationships in a database view.
Figure 2:
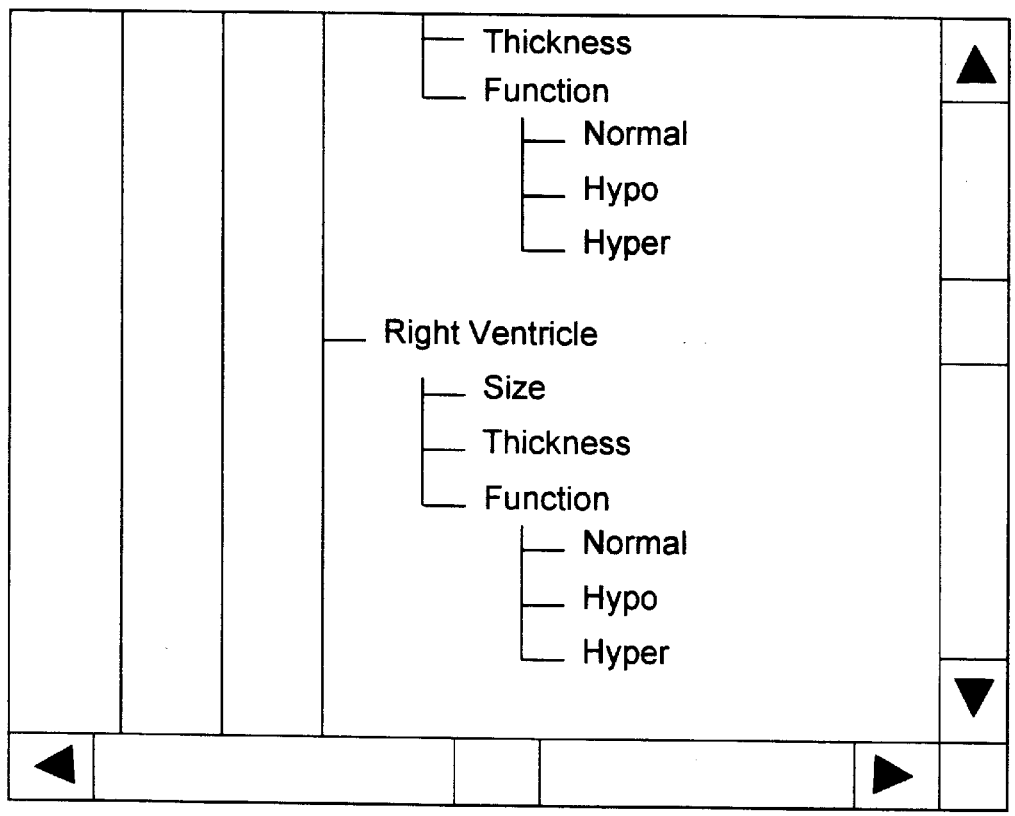
FIG. 2 is a schematic diagram of a computer screen showing how a first prior art technique might be used to navigate the hierarchical database view depicted in FIG. 1.
Figure 3A:
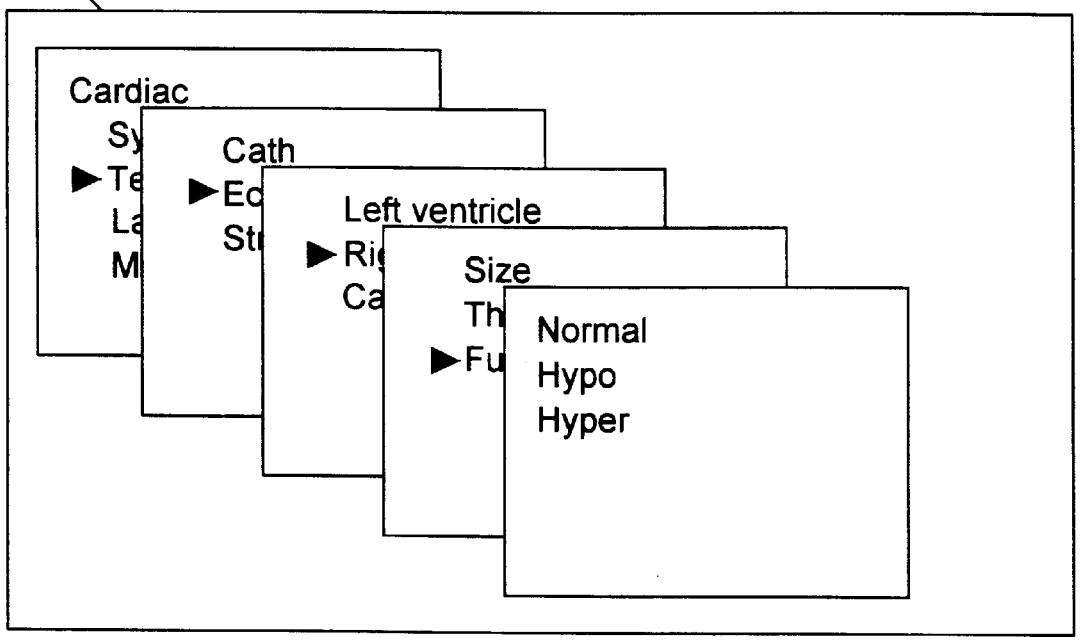
FIGS. 3a and 3b are schematic diagrams of a computer screen showing how a second prior art technique might be used to navigate the hierarchical database view depicted in FIG. 1.
Figure 3B:
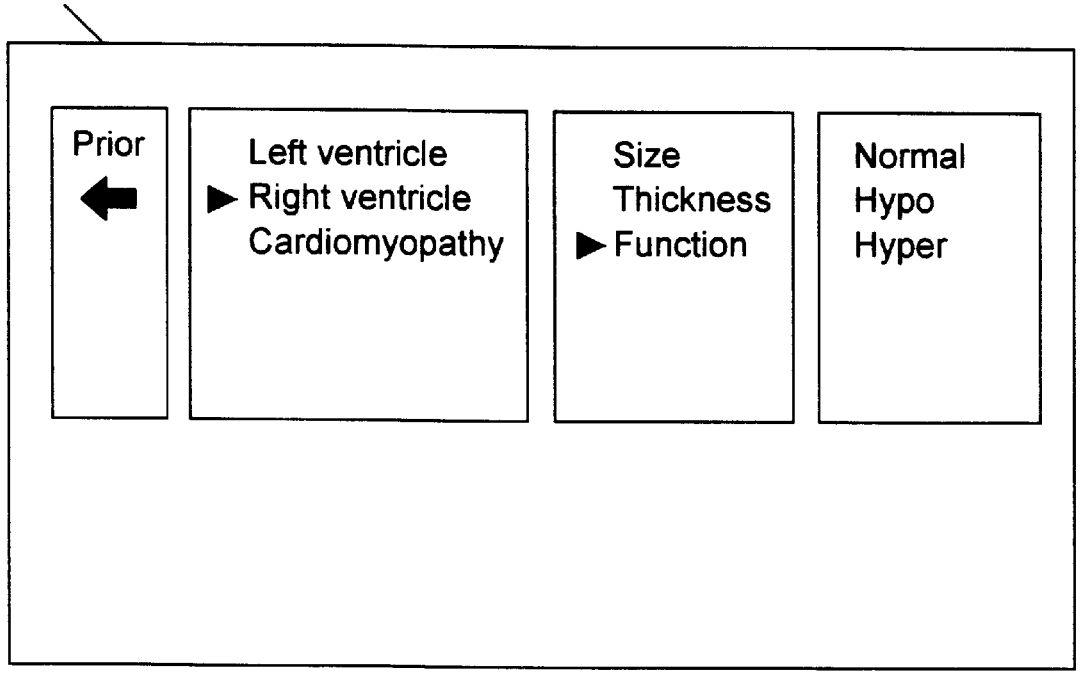
Figure 4:
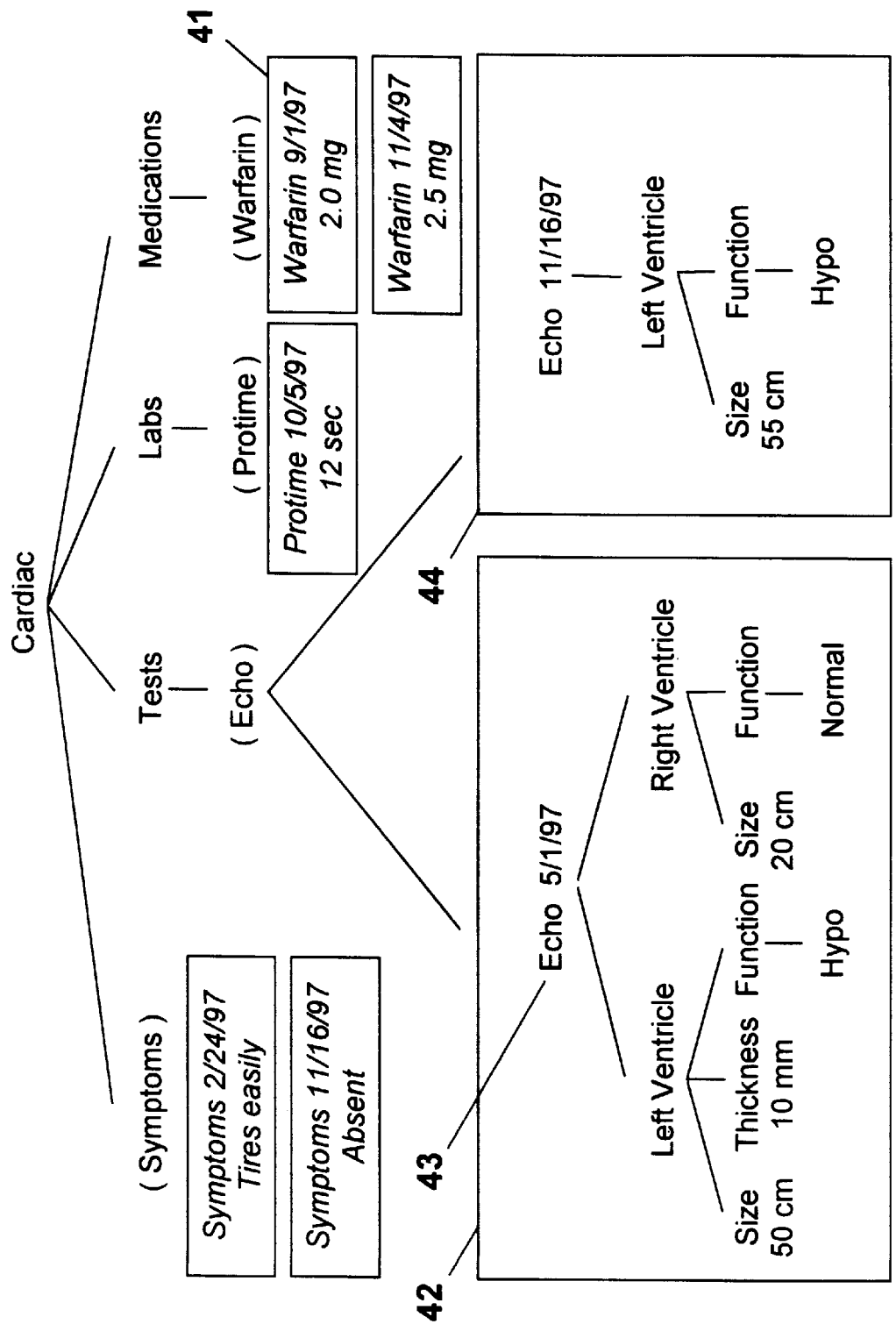
FIG. 4 is a diagram showing a set of node and subtree instances (database contents) for the database view depicted in FIG. 1.

In presenting a detailed description of the preferred embodiment of the invention, we will make use of examples based on a very simple clinical database. These examples are provided to illustrate certain elements of the invention. They are not to be construed as limiting the invention in any way.

In the preferred embodiment of the invention, each node in the tree representing a database view is assigned a unique identifier that encodes the path from the root node to that node. The nodes themselves are stored as a set of tuples (FIG. 5), with each tuple containing a node's identifier 51, a label 52, a descriptive phrase 53, the type of node (e.g., number, date, dose, text, file name, URL, etc.) 54, and a flag indicating whether the node automatically triggers the opening of an instance 55. This set of tuples completely describes the structure of the tree. Note that neither the tuple representation scheme, nor the node identification scheme is novel. Nor are these schemes required by the invention. Other embodiments of the invention could be easily constructed using different methods for representing a hierarchically-organized database view.

The instances (database contents) are stored using two sets of tuples: results and events (FIG. 6). Each tuple in the event tuple set 61 consists of an event identifier 62, the identifier of the corresponding node 63, and a date 64. The result tuple set 68 contains the data values themselves. Each tuple in this set consists of a node identifier 69, the identifier of the associated event 610, and a result (value) 611.

The purpose of the result tuple set is to record the entries made by the user. The event tuple set serves two purposes. First, it stores the date stamps that distinguish instances from one another. Referring to the example, FIGS. 6a and 6b show two instances of the Warfarin node. The instance corresponding to a Warfarin dose of 2.0 mg (617) is associated with event tuple 3 (66) and thus is date-stamped as occurring on 9/1/97. The instance corresponding to a Warfarin dose of 2.5 mg (618), on the other hand, is date stamped 11/4/97 because it is associated with event tuple 5 (67). In addition to providing a date stamp, event tuples are used to group data values that occur in the same subtree instance. In the example shown in FIG. 6, the result tuples corresponding to the phrases "LV size 50 cm" 612, "LV thickness 10 mm" 613, "LV function hypokinetic" 614, "RV size 20 cm" 615, and "RV function normal" 616 are all associated with event tuple 2 65 indicating that this subtree instance was recorded as part of the echocardiogram given on 5/1/97 (the node identifier "122" in event tuple 2 is the identifier of the Echo node 43 that is the root of this subtree instance 42). Note that the event and tuple representation schemes are not required by the invention. Other embodiments of the invention could be easily constructed using different methods for representing and storing the database contents (instances).

Figure 7:
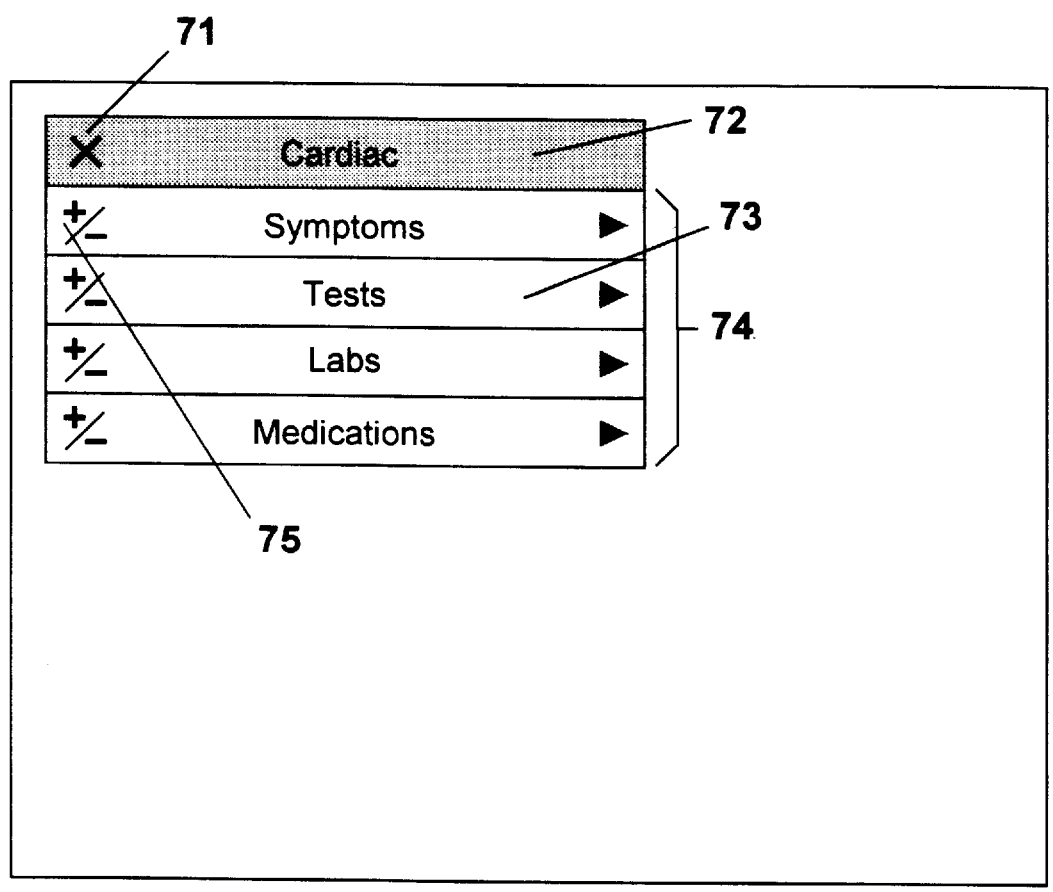
FIG. 7 is a schematic diagram of a computer screen showing the initial data navigation structure generated by the preferred embodiment of the present invention for the database view depicted in FIG. 1.

FIG. 7 is a screen representation of the initial navigation display created by the preferred embodiment of the invention. This display consists of a set of buttons: one button 72 corresponding to the root node of the database view (1 in FIG. 1) and a set of buttons 74 corresponding to the root node's children (2 in FIG. 1). These buttons are displayed below the root node's button and each is labeled with the corresponding node's label.

Figure 8:
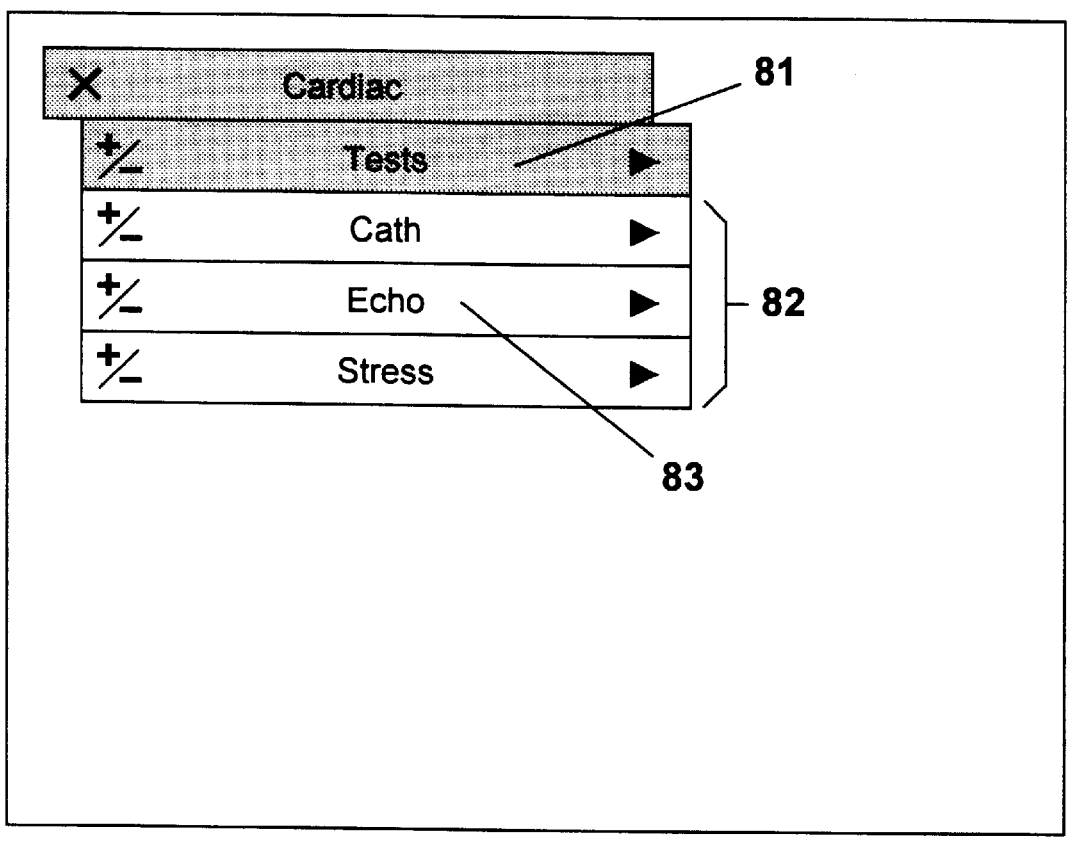
FIG. 8 is a schematic diagram of a computer screen showing how the data navigation structure is changed by the invention as the user moves downward in the database hierarchy.

The user begins the data entry process by selecting from among the child buttons using a mouse, pen, or other pointing device; by entering input from the keyboard; or by issuing voice commands. When a child button is selected, the display is updated, as shown by the following example: selecting the button labeled "Tests" 73 in FIG. 7, produces the display shown in FIG. 8. The buttons for the root node's children are erased and are replaced by the button the user selected 81. A new set of buttons is then displayed 82—one button for each of the children of the selected node. In the preferred embodiment of the invention, these buttons are displayed below the root node button and offset slightly to the right—however, this offset is not necessary.

Figure 9:
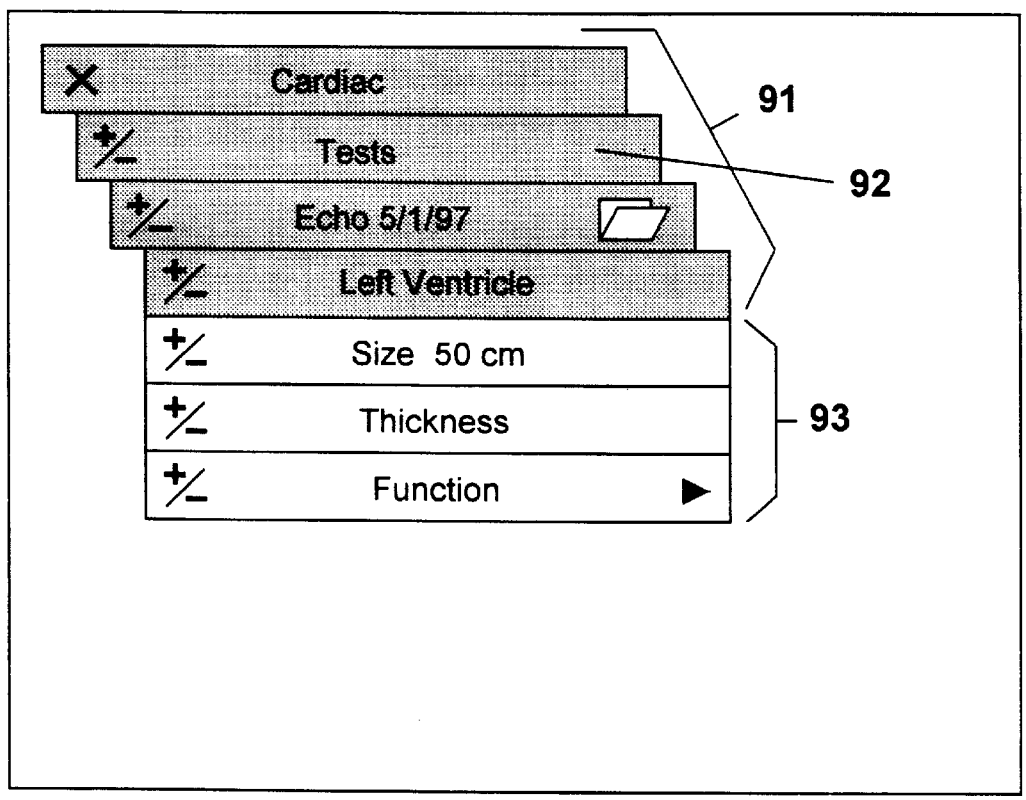
FIG. 9 is a schematic diagram of a computer screen showing how the data navigation structure is changed by the invention as the user moves downward in the database hierarchy.

Movement further down the hierarchy continues in this same manner. At each step, a button is selected from among the latest set of choices. This button is retained, the other choices are erased, and the selected button's children are displayed. FIG. 9 shows a screen representation of the display resulting from continued movement down the hierarchy. Note that the display contains a set of buttons for the current choices 93 and a set of buttons that corresponds to the path from root node to these choices 91. In the preferred embodiment of the invention these sets are displayed using visual cues to further differentiate them (black on white for the current choices, reverse video for the path to these choices).

The path buttons 91 are used to move back up the hierarchy. At any time, the user can select one of these buttons, at which point the display is updated as follows: All of the buttons that lie below the selected button (or, more precisely, all of the buttons that lie in the subtree below the node that corresponds to the selected button) are erased and a new set of buttons is displayed—one button for each of the children of the selected node. In effect, the display is restored to that which existed when the selected button was initially chosen on the way down the hierarchy. For example, selecting the Tests button 92, restores the display to that shown in FIG. 8. Everything below the Tests button 92 is erased and the Tests node's children 82 are redisplayed. The user is then free to continue down another path in the tree by selecting the appropriate child button.

In the present invention, instances are created and updated within the framework of the navigation process and display described above. In the preferred embodiment of the present invention, instances are created as follows: The user first opens an instance—that is, creates an event tuple. She then creates the result tuples that form the instance. These result tuples are automatically associated with the event tuple.

Instances can be opened automatically or manually. We will consider the automatic case first. Each node tuple (FIG. 5) contains a flag 55 that indicates whether the node automatically triggers the opening of an instance. Selecting a button that corresponds to a node for which this flag is marked "Auto" triggers the opening of an instance of the subtree that has this node at its root. Referring to the example (FIG. 8); selecting the Echo button 83 triggers the opening of an instance of the Echo subtree—that is, the subtree which has the Echo node at its root—because the Echo node's instance flag 56 is marked as "Auto" (FIG. 5).

Figure 10:
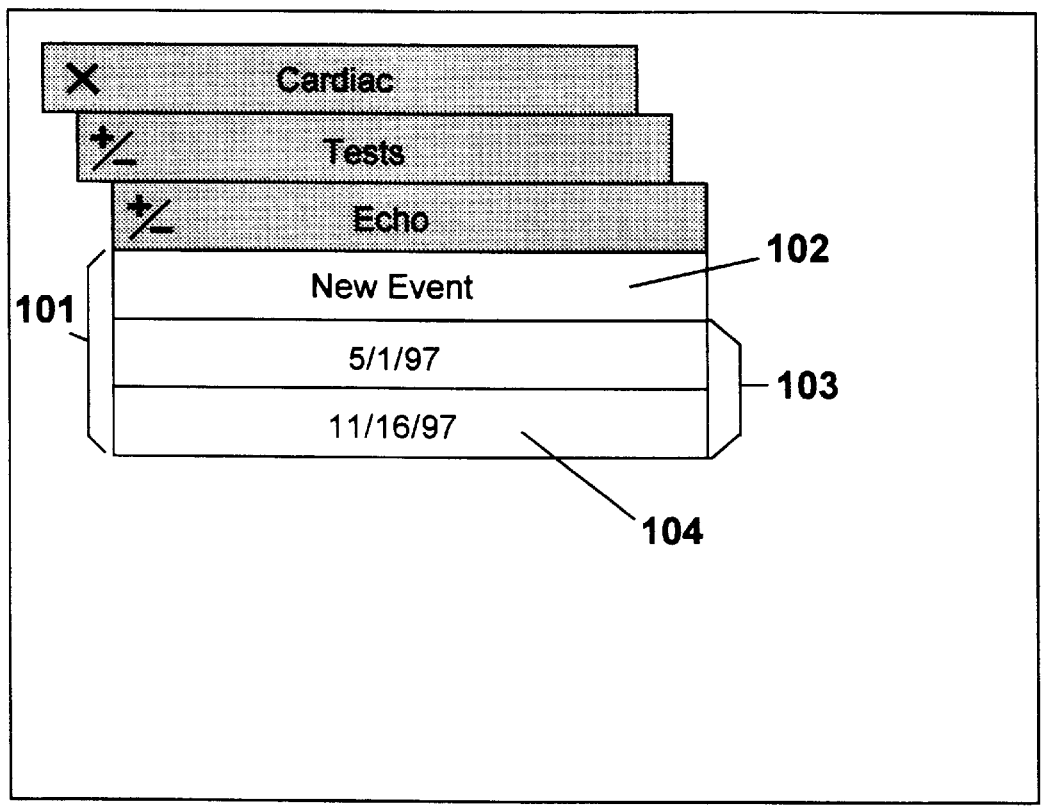
FIG. 10 is a schematic diagram of a computer screen instance selection tool.
Figure 11:
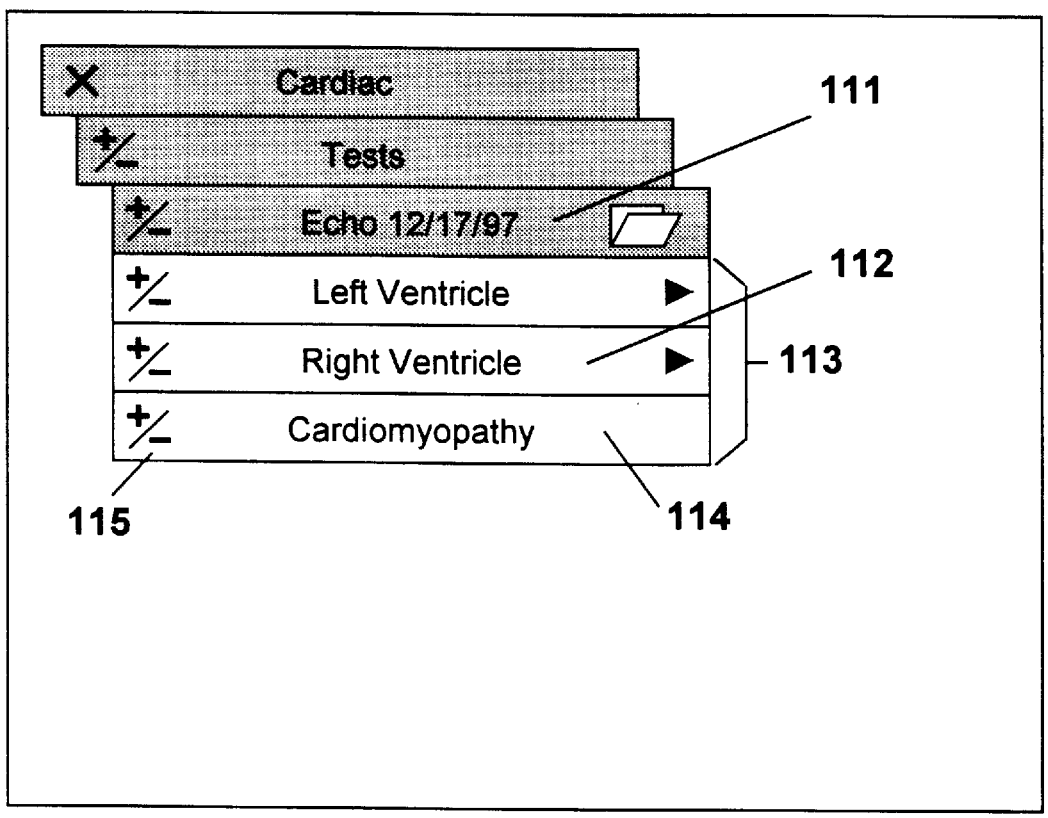
FIG. 11 is a schematic diagram of a computer screen representing the data navigation structure after an instance has been opened (selected).

When the opening of an instance is triggered, the instance selection tool 101 is displayed (FIG. 10). This tool contains a button labeled "New Event" 102 and a set of buttons 103 that correspond to previously entered instances of this subtree. Selecting the New Event button 102 initiates the display of a calendar tool into which the user inputs the date stamp for the new instance. This date stamp is then used to create a new event tuple to which subsequent results tuples will be associated and the display is modified as follows (FIG. 11): The Echo button 111 is updated to include the specified date stamp and buttons corresponding to the Echo node's children are displayed 113. For example, selecting the New Event button 102 in FIG. 10 and entering the date "12/17/97" adds the tuple (8,122,12/17/97) to the event tuple set and produces the display depicted in FIG. 11.

Once an instance has been opened, data values can be entered and stored in the result tuple set. This can be done in several ways depending on the type of node.

If a node is a finding—that is, a leaf node that does not require an input value, but that is simply chosen—then selecting the button corresponding to the node results in the creation of a result tuple for that node. Referring to the example begun above, selecting the Cardiomyopathy button 114 results in the addition of the tuple (1223, "Cardiomyopathy",8) to the result tuple set, where event tuple 8 specifies the open instance of the Echo subtree. Negative information (the absence of a symptom, for instance) can be recorded using the "−" button. For example, selecting the Cardiomyopathy "−" button 115 results in the addition of the tuple (1223,"No cardiomyopathy",8) to the result tuple set.

Figure 12A:
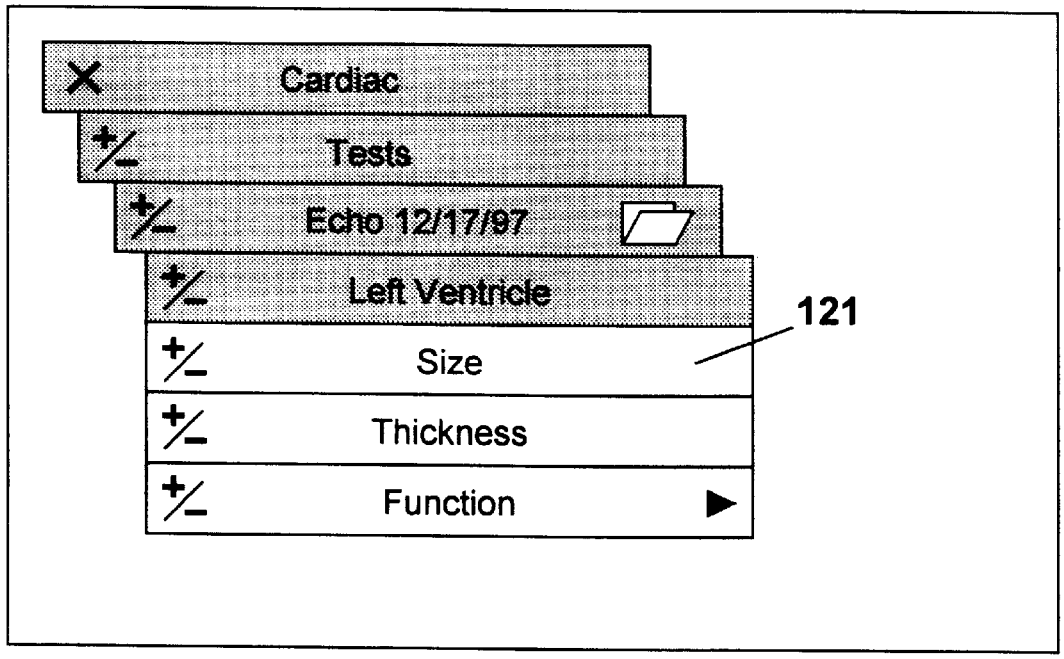
FIGS. 12a and 12b are schematic diagrams of a computer screen representing the data navigation structure before and during the recording of information about an open instance.
Figure 12B:
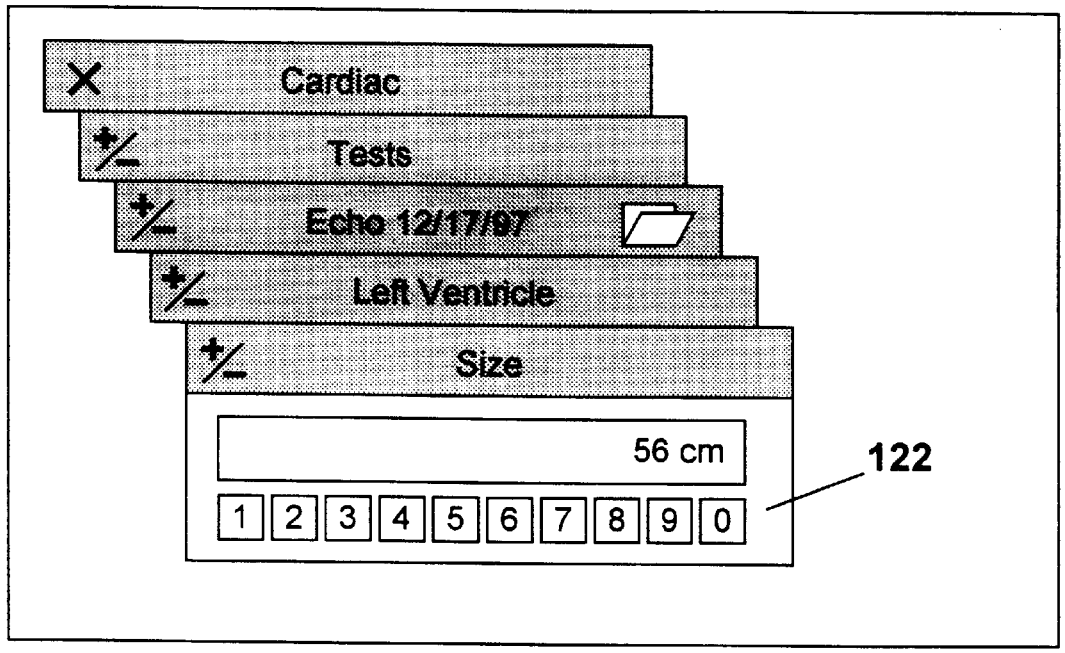
Figure 13:
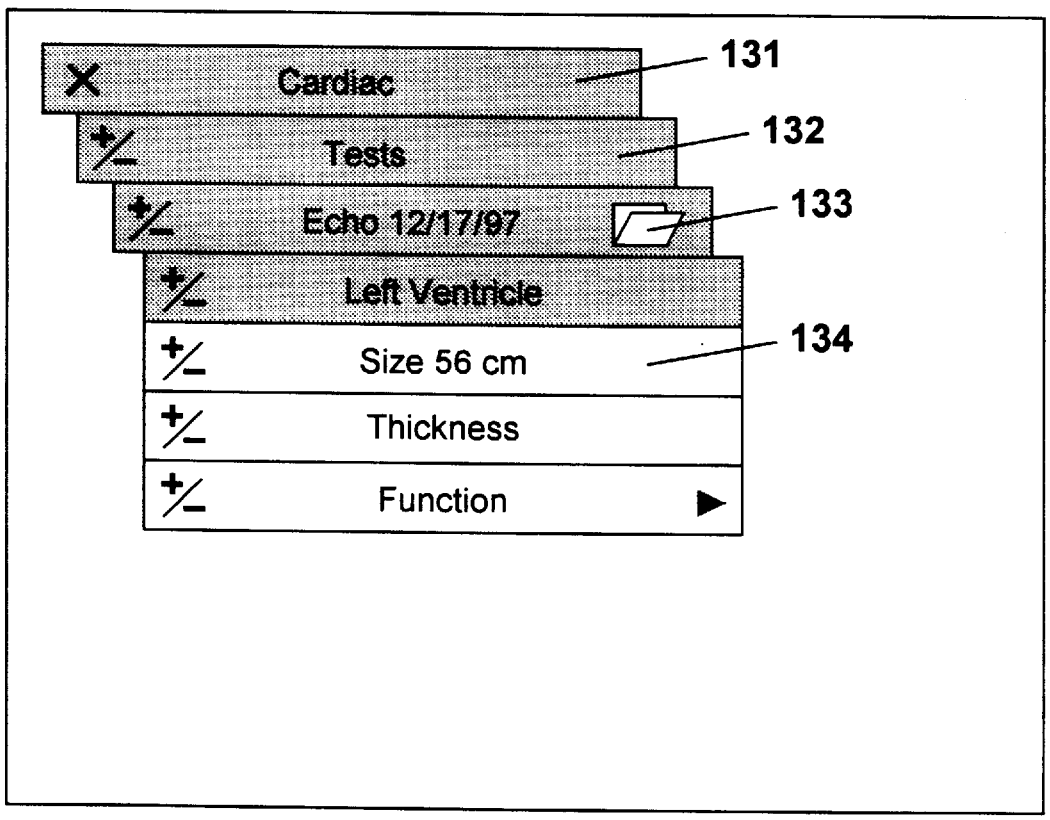
FIG. 13 is a schematic diagram of a computer screen representing the data navigation structure after the recording of information about an open instance.

If a node is a designated type (e.g., number, date, dose, URL, free text), then selecting the button corresponding to the node results in the display of the specialized input tool for that type of data. In the preferred embodiment of the present invention these tools are designed to fit within the physical constraints of the data navigation structure. Once the user has input a value, a result tuple is created for that node using the input value. The input tool is then erased, the input value is displayed on the button, and the data entry process continues. Referring again to the example (FIG. 12), selecting the Size button 121 results in the display of a number input tool 122. If the user inputs the number "56", then the tuple (12211,"LV size 56 cm",8) is added to the result tuple set. The Size button 134 is then modified by the addition of the result value "56 cm" (FIG. 13). In this way, the navigation structure can be used both to enter data and to provide feedback to the user regarding previously entered data.

Note that the various button markings (labels, recorded values, and so forth) are restored each time a button is displayed. For example, selecting the Echo and Left Ventricle buttons in succession will repeat the progression down the hierarchy performed above and will restore the display to that shown in FIG. 13.

Figure 14:
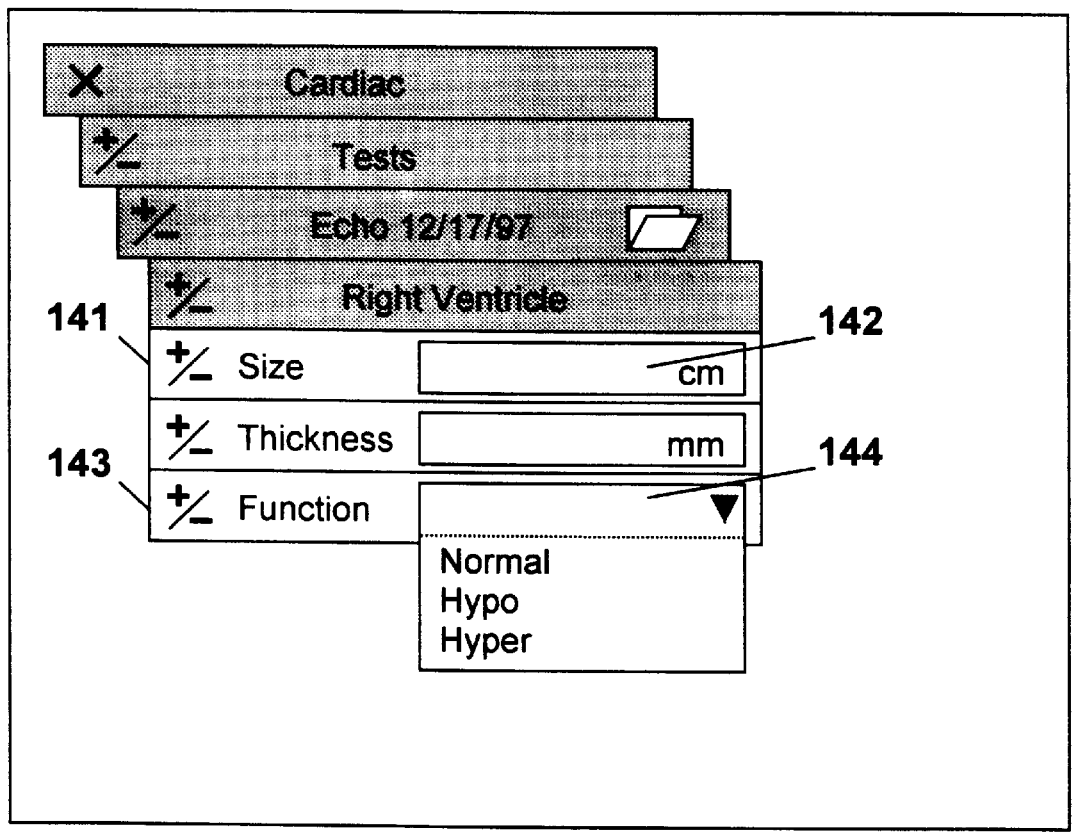
FIG. 14 is a schematic diagram of a computer screen representing a set of input forms embedded within the data navigation structure.

The invention includes support for hierarchically-structured forms-based data entry. In the preferred embodiment of the invention, a node can be designated as a "form" node. When a form node is selected, its children's buttons include concise "fill in the blanks" input boxes that are embedded within the navigation structure and into which the user can enter data. For example, if the node corresponding to the Right Ventricle button 112 is a form node, then selecting this button generates the display shown in FIG. 14. The Size button 141 requires numeric input and thus incorporates a numeric input box 142 into which the user can enter a numeric value. Nodes that have children generate a selection box (or combo box) that is populated with these children. For example, the Function button 143 corresponds to the Right Ventricle Function node (3 in FIG. 1), which has three children: Normal 4, Hypo 5, and Hyper 6 (in FIG. 1). These children provide the options listed in the Function button's selection box 144 (shown with the box expanded to reveal the options). The user then selects from among these options.

The present invention also provides for the inclusion of free text comments, graphics, and voice annotations about a node or, more precisely, about the subtree rooted at a node—as well as the inclusion of the names of related data files and the URLs of related HTML documents. This allows the invention to integrate multiple data sources by combining structured information (entered by the user via the data entry process described above) with unstructured commentary and links to supporting materials. In the preferred embodiment of the invention, freeform input is limited to text. Voice and graphical annotations are obvious extensions to this embodiment, however.

Figure 15:
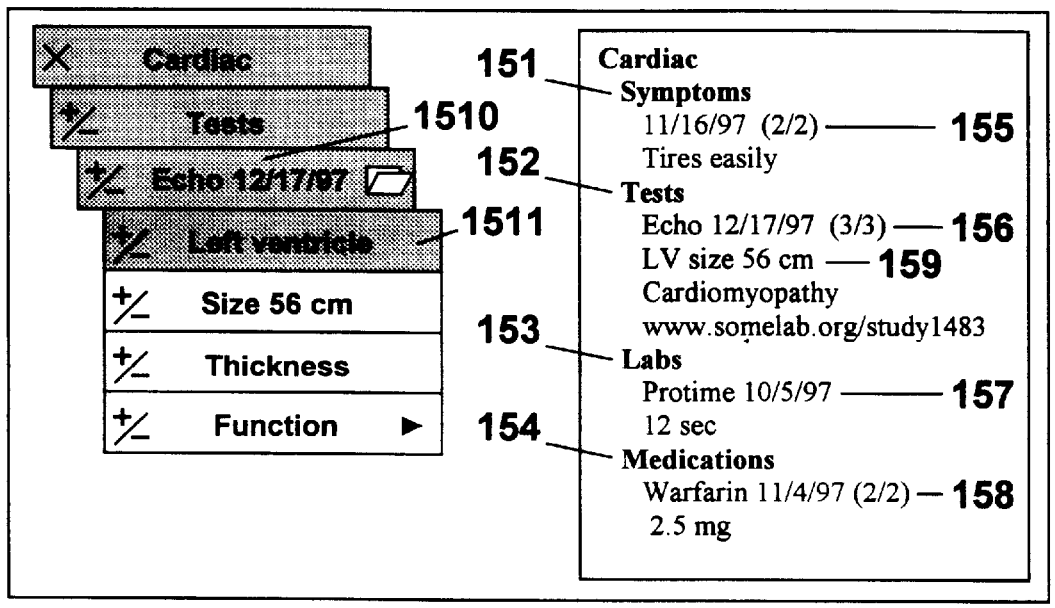
FIG. 15 is a schematic diagram of a computer screen representing a summary report generated by the preferred embodiment of the present invention.

In the preferred embodiment of the present invention, a report summary listing the information stored on a patient is automatically generated and updated as data is entered (FIG. 15). This report displays the stored information in a structured form in which the recorded subtree instances 155, 156, 157, 158 are shown within appropriate categories 151, 152, 153, 154. All of the information recorded about an instance is displayed, including, all findings and results, as well as any text commentary, file names, and URLs.

The data entry navigation process can be controlled (in part) from within the report summary. Selecting an entry in the report unrolls the navigation structure to the node associated with selected report entry. Referring back to the example, selecting the entry "LV size 56 cm" 159 in the report display results in the navigation structure opening automatically to reveal the Left Ventricle Size button 1511—including opening the Echo subtree instance for 12/17/97 1510.

In the present invention, an instance is closed whenever the user selects a button that is higher in the hierarchy than the button that corresponds to the root of the instance subtree. For example, selecting the Tests button 132 in FIG. 13 closes the Echo subtree instance corresponding to event tuple 8 (Echo 12/17/97). This results in a return to the display shown in FIG. 8. Similarly, selecting the Cardiac button 131 results in a return to the display shown in FIG. 7. A new instance must then be opened before any new information can be recorded.

An instance can also be closed using the "instance folder" button 133. Selecting this button closes the current instance and prompts the user to open another instance of the same subtree. Referring back to the example, selecting the Echo node's "instance folder" button 133 closes the current Echo subtree instance (event tuple 8) and results in a return to a display similar to that shown in FIG. 10 (with the addition of the event "Echo 12/17/97"), at which point the user is prompted to open another (new or existing) instance of the Echo subtree.

The invention also allows instances to be opened manually. In the preferred embodiment of the invention, if an instance is not already open, then selecting a node's "+" or "−" button will manually trigger the opening of an instance of the subtree rooted at that node. Selecting the Symptoms button's "+" button 75 (FIG. 7), for instance, results in the display of the instance selection tool for the Symptoms node. The user then opens a subtree instance whose root is the Symptoms node in precisely the same manner as was done with the Echo node above. For example, entering the date 12/21/97 would add the tuple (9,11,12/21/97) to the event tuple set. The user could then add information about the patient's cardiac symptoms to this open Symptoms instance using the processes outlined above.

Once an instance has been closed, the information associated with the instance can be updated by simply reopening the instance and adding new results or deleting existing results. Referring back to the example, selecting the button labeled with the date "11/16/97" 104 in FIG. 10 will open the existing Echo subtree instance associated with the event tuple (7,122,11/16/97) for review and updating. New results can then be added using the processes described above.

Figure 16:
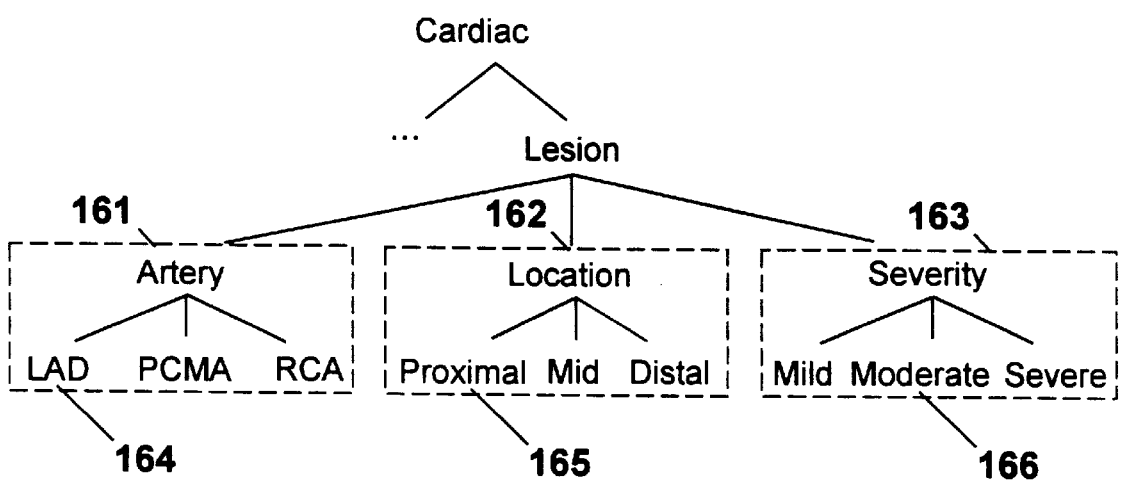
FIG. 16 is a schematic diagram showing the relationships in a database view in which multiple nodes are used to specify a single database entry.

Up to this point, we have assumed that each entry in the database corresponds to a single node in the database view. In many cases, it will be necessary—or, at a minimum, significantly more efficient—to synthesize a database entry based on information from several nodes in the database view. FIG. 16, for example, shows a simple coronary lesion subtree. Fully describing a single lesion requires selecting one node from each of the Artery 161, Location 162, and Severity 163 subtrees. The information in these nodes is then composed to form the database entry for a lesion. Collectively, for example, the LAD 164, Proximal 165, and Moderate 166 nodes specify the lesion "moderate stenosis of the proximal left anterior descending coronary artery" and it is this entry that is stored in the database. Note that in this case, the individual nodes are not meaningful unto themselves, but are only meaningful when included as part of the context in which they are embedded. For example, "Moderate Stenosis" is only meaningful when used within a context that includes an artery and a location.

Hierarchical database views of this form dramatically reduce the number of nodes required to represent a given set of database relationships. Converting the Lesion tree to one in which each database entry corresponds to a single node would entail placing the Severity subtree below each leaf node in the Location subtree and placing this nested Location/Severity subtree below each leaf node in the Artery subtree—thereby producing a tree with more than twice as many nodes ($3^3+1=28$ nodes, to be precise). Note that as options are added to the Artery, Location, and Severity subtrees, the size of this tree will increase exponentially. The Lesion tree shown in FIG. 16, on the other hand, will only increase linearly in size.

Figure 17A:
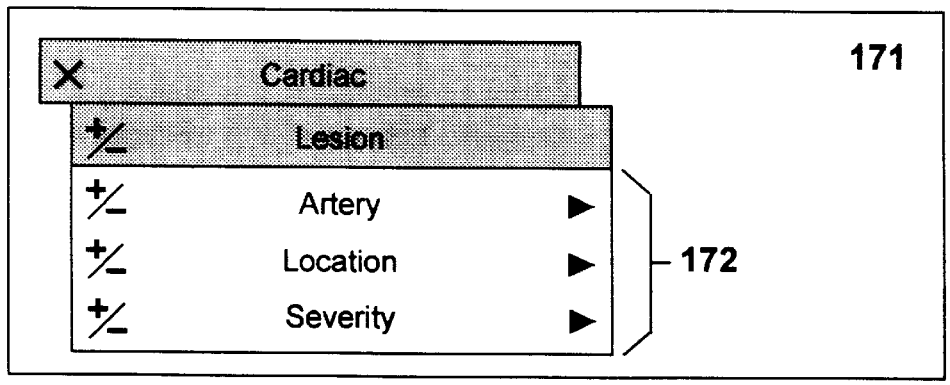
FIGS. 17a, 17b and 17c are schematic diagrams of a set of screen representations that show how values for multiple nodes are input and composed to form a single database entry.
Figure 17B:
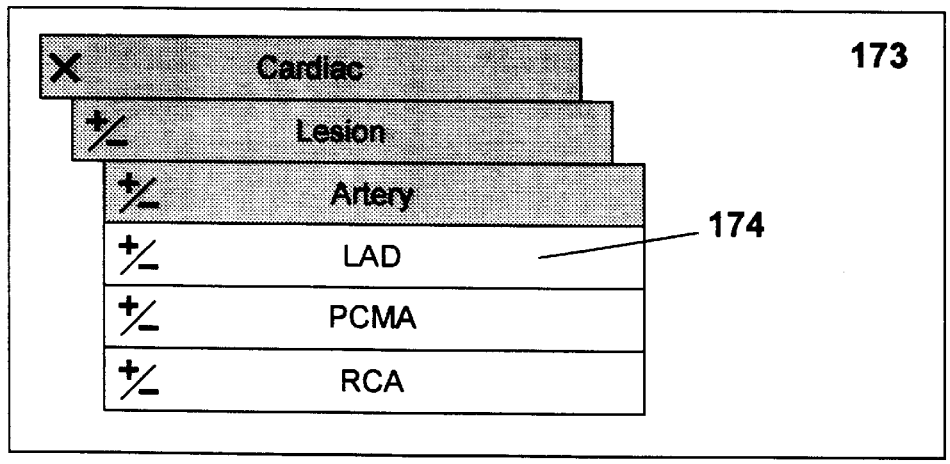
Figure 17C:
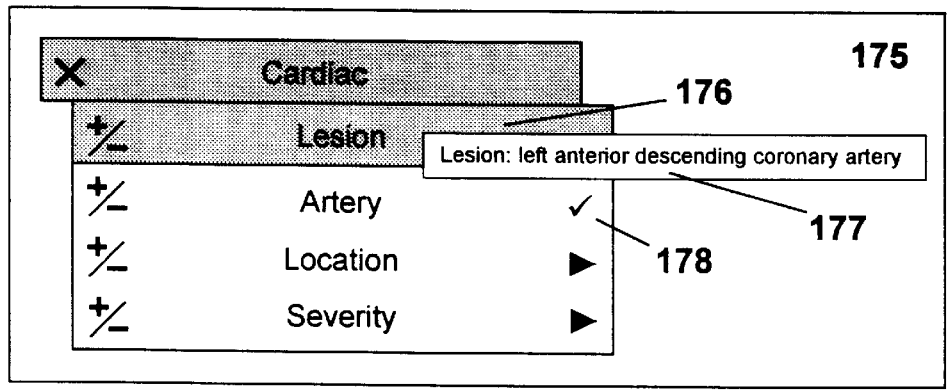

In the preferred embodiment of the present invention, nodes can be designated as "compound findings". Entering the data that comprises a compound finding is done by selecting one node in each of the subtrees of the compound finding node. FIG. 17 shows the display 171 generated from the Lesion subtree in FIG. 16. The buttons corresponding to the Lesion compound finding node's children 172 are grouped together to visually communicate that these buttons are part of a compound finding. Note that although there are no horizontal divisions between them, these are still separate buttons. Navigation further down the hierarchy 173 proceeds in precisely the manner discussed above, with one significant exception: as soon as a result is selected within a subtree—say, for instance, the user selects the LAD button 174—control immediately returns back to the compound finding level 175. A checkmark 178 is used to indicate that a value has been selected for the Artery subtree and the phrase "Lesion: left anterior descending coronary artery" is displayed 177. The compound finding is recorded to the database (as a single result) either when a value has been selected for each of the subtrees or when the user selects a button above the Lesion button 176 that delineates the compound finding.

Figure 18A:
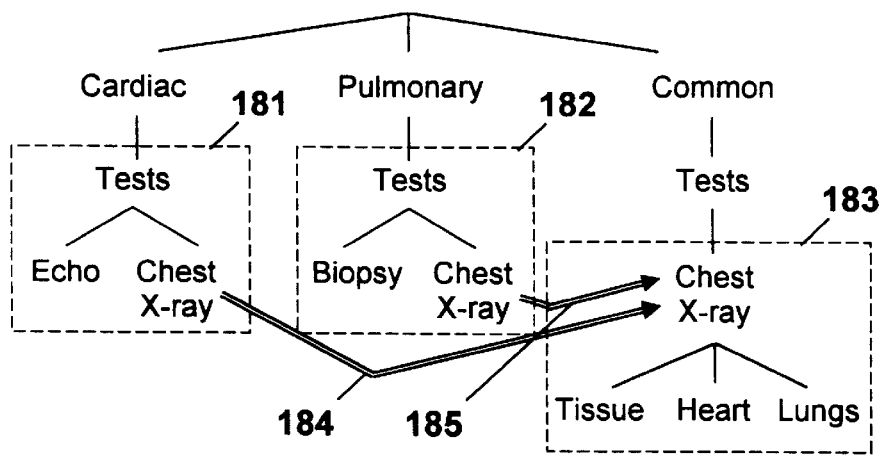
FIGS. 18a, 18b and 18c are schematic diagrams of a database view that includes serial links (FIG. 18a) and a pair of screen representations (FIGS. 18b and 18c) that show how a serial link is presented and traversed by the invention.
Figure 18B:
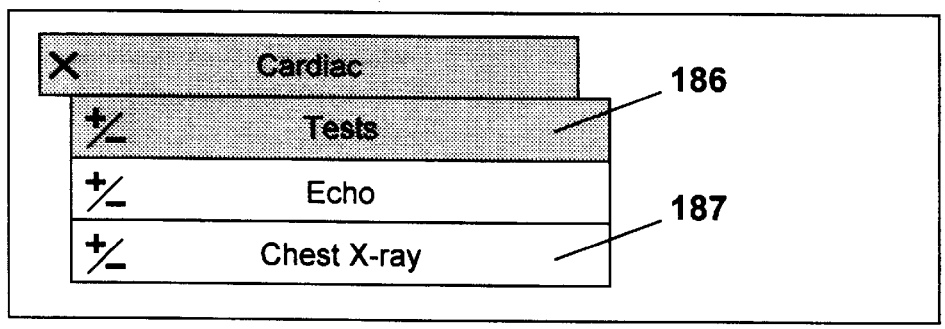
Figure 18C:
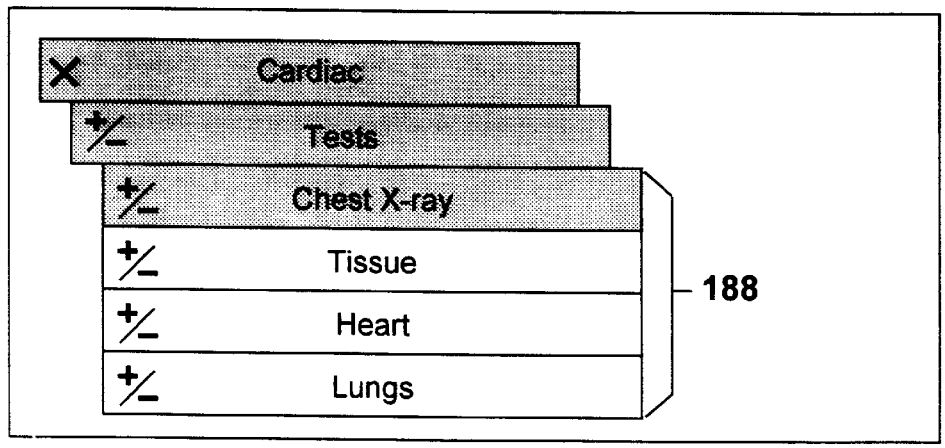

The present invention also supports database views that are not pure hierarchies, but which contain multiple paths between nodes (or hierarchies). Such views are referred to as directed acyclic graphs and are commonly used in database systems to reduce the need for the entry (and storage) of redundant data and to allow data to be viewed within multiple contexts. The database view shown in FIG. 18, for example, contains the Chest X-ray hierarchy 183 within both the Cardiac Tests 181 and Pulmonary Tests 182 hierarchies reflecting its use in diagnosing conditions in both medical specialties.

In the preferred embodiment of the present invention, these non-hierarchical links 184, 185 are represented using a designated set of serial links. Whenever a node that is the source of a serial link is encountered, the serial link's target node is automatically displayed in place of the link's source node. Suppose, for example, that the user is entering information about Cardiac Tests 186. In this case, the Chest X-ray button 187 is automatically associated with the root node of the Chest X-ray subtree 183 that is the target of the serial link 184. Selecting the Chest X-ray button 187 results in the display of a set of buttons 188 that correspond to the children of the root node of the Chest X-ray hierarchy 183. Similarly, if the user were to encounter Chest X-ray within the Pulmonary Tests hierarchy, the Chest X-ray hierarchy would be displayed as though it were part of Pulmonary Tests. Note that information recorded as part of the Chest X-ray hierarchy can be reviewed or updated at a later date using either the Cardiac Tests or Pulmonary Tests hierarchy—regardless of which hierarchy was originally used to record the Chest X-ray data.

The present invention also supports the parallel traversal of multiple branches. These parallel traversals can be triggered automatically (as parallel navigation structures), thereby providing a means for signaling that a relationship exists between data items and a method for reviewing related data items in context.

In the preferred embodiment of the invention, a designated set of parallel links is maintained. Whenever a node that is the source of a parallel link is traversed, a new navigation structure that contains the link's target node is automatically displayed beside the original navigation structure. The user is then free to move up and down either navigation structure. The new (parallel) navigation structure is closed (and no longer displayed) whenever the user selects a node that is higher in the hierarchy than the node that originally triggered the display of the parallel structure.

Figure 19A:
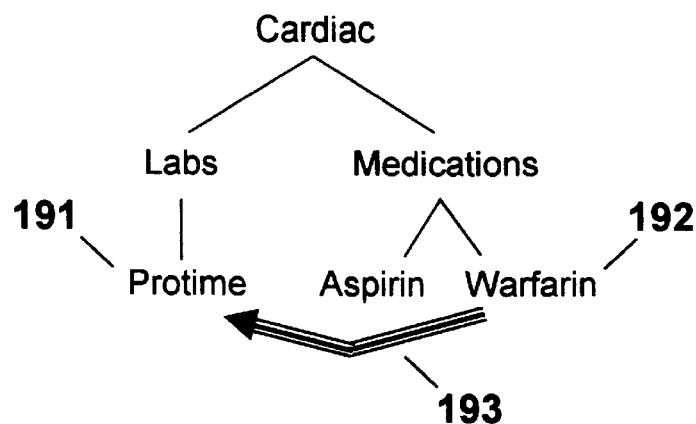
FIG. 19a is a schematic diagram showing a database view that includes a parallel link.
Figure 19B:
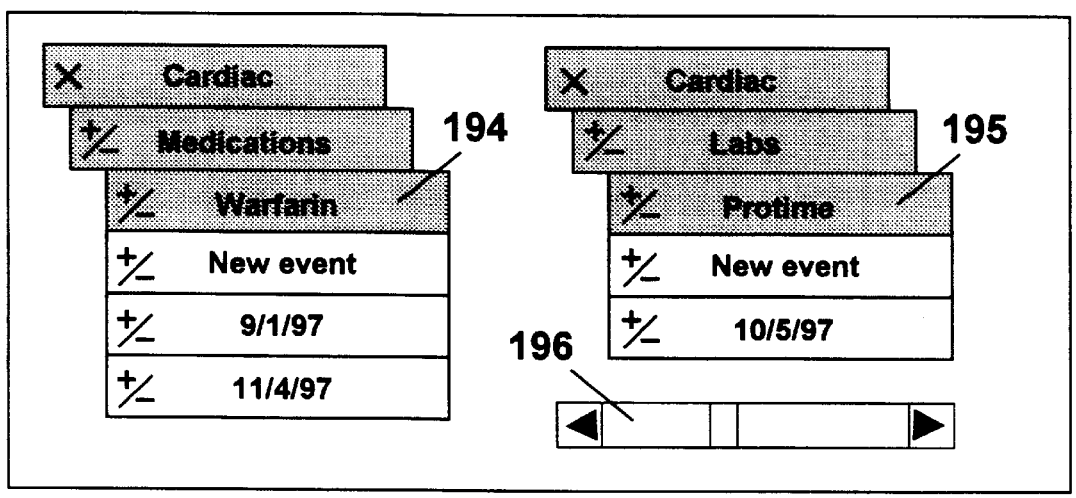
FIG. 19b is a schematic diagram of a screen showing how a parallel link is presented and traversed by the invention.

The database view shown in FIG. 19, for example, includes a parallel link 193 from the Warfarin node 192 to the Protime node 191 reflecting the relationship between the medication Warfarin and the laboratory test for Protime. Whenever the user traverses the Warfarin node 194, the navigation structure containing the Protime node 195 is automatically generated. Selecting a node above the Warfarin node 194 automatically closes the Protime navigation structure 195. Note that a node can be the source of multiple parallel links. However, in the preferred embodiment of the invention, only one parallel navigation structure is displayed at a time. The user moves between the parallel navigation structures using a simple slider control 196.

The methods forming the present invention are depicted in pseudocode form in FIG. 20 and FIG. 21.

The navigate() function 201 controls the generation and processing of the navigation structure. Assignment statements 202 initialize path set P={root node of the database view} and child set C={children of the root node}. Loop-until structure 203 then makes repeated calls to the generate_structure() function 204, with each call reflecting user-initiated changes in set P, set C, and the underlying database (i.e., the event and result tuple sets). These calls terminate when the user selects the Close button on the root node 71.

The generate_structure() function 204 creates the navigation structure for the current set of path nodes (P) and child nodes (C). For-loop structure 205 displays the cascading set of buttons—one button for each node in set P. The buttons are displayed one below the other, with each button slightly offset to the right from the button above For-loop structure 206 displays a linear set of buttons—one button for each node in set C. The buttons are displayed in a column, one below the other. If a child node is the source of a serial link, then if-selection structure 207 replaces the child node with the node that is the target of the serial link. The remaining code then processes this target node in place of the child node. If-selection structure 208 displays a stored value on a button if the open subtree instance contains a result tuple for the corresponding node.

Loop-until structure 209 waits for the user to select a button. A call 2010 to the update_sets() function 211 is then made to update sets P and C in response to the button the user selected.

The update_sets() function 211 updates set P, set C, and the underlying database based on the button selected by the user (button_pressed) in the generate_structure() routine 204.

If-selection structure 212 determines whether the button selected corresponds to one of the path nodes (P). If it does, then assignment statement 213 truncates set P to include only those nodes leading up to and including the selected node. If-selection structure 214 then checks whether the button selected is above the root node of the open subtree instance. If so, then the open instance is closed and if selection structure 215 is used to close any parallel navigation structures that may also be open.

Else-if-selection structure 216 determines whether the button selected corresponds to one of the child nodes (C). If it does, then a variety of tests are performed to determine the consequences of selecting this child node. Note that the following tests are performed sequentially and are not mutually exclusive.

If-selection structure 217 determines whether the selected child node is an automatic trigger for opening an instance (based on the information in the corresponding node tuple). If it is, then the instance selection tool is displayed and a (new or existing) subtree instance is opened based on the input date. Note that this may entail creating a new event tuple or referencing an existing tuple. Assignment statement 218 moves the selected child node to the path set, assignment statement 219 creates a new child set containing the children of the selected node, and assignment statement 2110 marks the relative position of the selected node (which defines the open subtree instance) within the path set.

If the selected child node corresponds to a finding, then if-selection structure 2111 stores the corresponding result in the database (as a result tuple). If the selected child node corresponds to a predefined type, then else-if-selection structure 2112 displays the corresponding data input tool and stores the input value in the database (as a result tuple).

If-selection structure 2113 determines whether the selected child node has children of its own. If it does and if the selected child did not open a new instance through if-selection structure 217, then assignment statement 2114 moves the selected child node to the path set and assignment statement 2115 creates a new child set containing the children of the selected node.

Finally, if-selection structure 2116 checks whether the selected node is the source of a parallel link. If it is, then a new parallel navigation structure is displayed with path node set $Q=\{Q_1, Q_2, \ldots, Q_{k'}\}$ and child node set $D=\{D_1, D_2, \ldots, D_{m'}\}$, where $\{Q_1, Q_2, \ldots, Q_{k'-1}\}$ is the set of nodes on the path to the node $Q_{k'}$ that is the target of the parallel link and $\{D_1, D_2, \ldots, D_{m'}\}$ is the set of children of node $Q_{k'}$.

The foregoing disclosure of embodiments of the invention has been presented for the purpose of illustration and description. It is not intended to be exhaustive or to limit the invention to the precise forms disclosed. Many variations and modifications of the embodiments described herein will be obvious to one of ordinary skill in the art in light of the above disclosure. The scope of the invention is to be defined only by the claims appended hereto, and by their equivalents.

What we claim is:

1. A method for the entry, review and update of data in a hierarchically-organized database comprising:
    (a) creating the hierarchically-organized database, said database having a root node, said root node having at least one child node, and also having further descendant nodes;
    (b) displaying the root node and each of the at least one child nodes of the root nodes as a set of selectable buttons;
    (c) navigating the database by selecting one of the selectable buttons at a time;
    (d) retaining the display of only the selected button and its parent button, and displaying all of the child nodes associated with the selected node as selectable child buttons;
    (e) repetitively selecting said child buttons and erasing other child buttons, but retaining ancestor buttons in the display;
    (f) entering new data by selecting a selectable button for the input of new data pertaining to the currently displayed node; and
    (g) generating a report from the hierarchically-organized database integrating the entered data into a structured summary of the entered data.

2. The method of claim 1, wherein step (e) is repeated until leaf buttons are displayed.

3. The method of claim 1, with each node being stored as a set of tuples, wherein each tuple comprises a node identifier, a label, and a descriptive phrase.

4. The method of claim 3, wherein at least one of said tuples comprises a type of node.

5. The method of claim 3, wherein at least one of said tuples comprises a flag that indicates whether the node automatically triggers the opening of an instance.

6. The method of claim 1, wherein the selection of a selectable ancestor button results in the removal of all descendant selectable buttons of said ancestor and the redisplay of the selectable buttons representing the child buttons of said ancestor.

7. The method of claim 1, further comprising displaying the data value from an associated data instance as part of the selectable button.

8. The method of claim 1, wherein multiple data instances associated with a database node are displayed as selectable child buttons of the button corresponding to the database node.

9. The method of claim 1, wherein multiple data instances are selectable for modification and deletion.

10. The method of claim 1, further comprising linking pairs of nodes to form a directed acyclic graph such that the display of one node in a linked pair triggers the display of the selectable button associated with the link's target node in place of the link's source node.

11. The method of claim 1, further comprising linking pairs of nodes to form a directed acyclic graph such that the selection of one node in a linked pair triggers the display of a separate navigation structure containing a selectable button corresponding to the link's target node.

12. The method of claim 1, wherein said database is a database of medical information.

13. The method of claim 1, wherein said new data is represented by a selectable button integrated into the previously-entered data instances associated with the displayed node.

14. The method of claim 1, further comprising selecting a button for entering a negative data instance to represent the absence of a particular finding or state.

15. The method of claim 1, further comprising selecting a button for entering freeform text information.

16. The method of claim 1, further comprising a selecting a button for entering audio data.

17. The method of claim 1, further comprising selecting a button for entering graphical data.

18. The method of claim 1, further comprising selecting a button for the entering hyperlinks to related data.

19. The method of claim 1, further comprising displaying input boxes as part of certain selectable buttons and entering data using these boxes.

20. The method of claim 1, further comprising the composition of multiple input data buttons to form a single database entry.

21. The method of claim 1, further comprising simultaneously displaying data in a separate report summary window.

22. The method of claim 21, further comprising displaying data instances as selectable data buttons, such that selecting a data button in the report display initiates the display of said data button as a selectable button along with selectable buttons corresponding to the ancestors and children of said data button.

23. A hierarchically-organized database system comprising:
    (a) means for creating the hierarchically-organized database having a root node, said root node having at least one child node and also having further descendant nodes;
    (b) means for displaying the root node and each of the at least one child nodes of the root nodes as a set of selectable buttons;
    (c) means for navigating the database by selecting one of the selectable buttons at a time;
    (d) means for retaining the display of only the selected button and its parent button, and displaying all of the child nodes associated with the selected button as selectable child buttons;
    (e) means for repetitively selecting said child buttons and erasing other child buttons, but retaining ancestor buttons in the display;
    (f) means for entering new data by selecting a selectable button for the input of new data pertaining to the currently displayed node; and
    (g) means for generating a report from the hierarchically-organized database integrating the entered data into a structured summary.

24. The system of claim 23, wherein step (e) is repeated until leaf buttons are displayed.

25. The system of claim 23, wherein the selection of a selectable ancestor button results in the removal of all descendant selectable buttons of said ancestor and the redisplay of the selectable buttons representing the child buttons of said ancestor.

26. The system of claim 23, further comprising means for displaying the data valve from an associated data instance as part of the selectable button.

27. The system of claim 23, wherein the multiple data instances associated with a database node or subtree are displayed as selectable child buttons of the button corresponding to the database node.

28. The system of claim 27, wherein each node is stored as a set of tuples, and wherein each tuple comprises a node identifier, a label, a descriptive phrase, and an associated sentence or sentence fragment.

29. The system of claim 28, wherein at least one of the tuples comprises a type of node.

30. The system of claim 27, further comprising linking pairs of nodes to form a directed acyclic graph such that the display of one node in a linked pair triggers the display of the selectable button associated with the link's target node in place of the link's source node.

31. The system of claim 23, further comprising means for linking pairs of nodes to form a directed acyclic graph such that the selection of one node in a linked pair triggers the display of a separate navigation structure containing a selectable button corresponding to the link's target node.

32. The system of claim 23, further comprising means for selecting a button for entering a negative data instance to represent the absence of a particular finding or state.

33. The system of claim 23, further comprising means for selecting a button for entering free-form text information.

34. The system of claim 23, further comprising means for a selecting a button for entering audio data.

35. The system of claim 23, further comprising means for selecting a button for entering graphical data.

36. The system of claim 23, further comprising means for selecting a button for the entering hyperlinks to related data.

37. The system of claim 23, further comprising means for displaying input boxes as part of certain selectable buttons and entering data using these boxes.

38. The system of claim 23, further comprising means for forming multiple input data buttons into a single database entry.

39. The system of claim 23, further comprising means for simultaneously displaying data in a separate report summary window.

40. The system of claim 39, further comprising means for displaying data instances as selectable data buttons, such that selecting a data button in the report display initiates the display of said data button as a selectable button along with selectable buttons corresponding to the ancestors and children of said data button.

41. A method for navigating a hierarchically-organized database having a root node comprising:

(a) displaying the root node;

(b) displaying all child nodes of the root node as selectable buttons;

(c) selecting a first one of the child nodes of the root node to start navigating the database, thus prompting the display of the root node, the first one of the child nodes of the root node, and all child nodes of the first one of the child nodes as selectable buttons;

(d) moving down the database by selecting one of the children buttons of the selected button, erasing all other children buttons of the selected button, and displaying all the children buttons of the selected child buttons, but retaining the display of selected ancestor buttons;

(e) navigating the database by selecting selectable buttons representing nodes of the database, until leaf buttons are displayed; and (f) generating a report from the hierarchically-organized database integrating the entered data into a structured summary.

42. The method of claim 41, further comprising selecting buttons representing the absence of a particular finding or state.

43. The method of claim 41, further comprising selecting a button for entering audio data.

44. The method of claim 41, further comprising selecting a button for entering graphical data.

45. The method of claim 41, further comprising selecting a button for entering free-form textual data.

46. The method of claim 41, further comprising selecting a button for entering hyperlinks to related data.

47. The method of claim 41, further comprising displaying input boxes as part of certain selectable buttons, and entering data using those buttons.

48. The method of claim 41, further comprising displaying data instances as selectable data buttons, such that selecting a data button in the report display initiates the display of said data button as a selectable button along with selectable buttons corresponding to the ancestors and children of said data button.

49. The method of claim 41, wherein each node is stored as a set of tuples, and wherein each tuple comprises a node identifier, a label, a descriptive phrase, and an associated sentence or sentence fragment.

50. The method of claim 49, wherein at least one of said tuples comprises a type of node.

51. The method of claim 49, wherein at least one of said tuples comprises a flag that indicates whether the node automatically triggers the opening of an instance.

52. A method for navigating a database comprising:

(a) displaying a representation of the database as a set of buttons, wherein each button represents a node in the database;

(b) selecting a button, thus erasing the children buttons of the parent button, and displaying the children button of the selected button;

(c) moving down the database by selecting one of the children buttons of the selected button, erasing all the other children buttons of the selected button, and displaying all the children buttons of the selected child buttons and all the selected ancestor buttons;

(d) moving up the database by selecting an ancestor button, displaying all the children buttons of the ancestor button, and erasing all buttons that lie below the children buttons of the ancestor button; and (e) generating a report from the data entered in the database integrating the entered data into a structured report providing a summary listing of information entered with the selected buttons.

53. The method of claim 52, wherein all ancestor buttons going back to a root node button are displayed.

54. The method of claim 52, wherein each node is stored as a set of tuples, and wherein each tuple comprises a node identifier, a label, and a descriptive phrase.

55. The method of claim 54, wherein each node also comprises an associated sentence or sentence fragment.

56. The method of claim 54, wherein at least one of said tuples comprises a type of node.

57. The method of claim 54, wherein at least one of said tuples comprises a flag that indicates whether the node automatically triggers the opening of an instance.

58. The method of claim 52, further comprising linking pairs of nodes to form a directed acyclic graph such that the display of one node in a linked pair triggers the display of the selectable button associated with the link's target node in place of the link's source node.

59. The method of claim 52, further comprising linking pairs of nodes to form a directed acyclic graph such that the selection of one node in a linked pair triggers the display of a separate navigation structure containing a selectable button corresponding to the link's target node.

60. The method of claim 52, wherein said database is a database of medical information.

61. The method of claim 52, wherein said method is executed on a computer system having limited screen space available for display.

* * * * *

UNITED STATES PATENT AND TRADEMARK OFFICE
CERTIFICATE OF CORRECTION

PATENT NO. : 6,154,750
DATED : November 28, 2000
INVENTOR(S) : James ROBERGE et al.

It is certified that error appears in the above-identified patent and that said Letters Patent is hereby corrected as shown below:

TITLE PAGE:

[75] Inventors, line 1, change "Damen" to --Darien--.

Signed and Sealed this

First Day of May, 2001

Attest:

NICHOLAS P. GODICI

Attesting Officer     Acting Director of the United States Patent and Trademark Office